United States Patent [19]

Rao et al.

[11] Patent Number: 4,659,743

[45] Date of Patent: Apr. 21, 1987

[54] PROCESS AND CATALYST FOR CONVERTING SYNTHESIS GAS TO LIQUID HYDROCARBON MIXTURE

[75] Inventors: V. Udaya S. Rao, Monroeville; Robert J. Gormley, Pittsburgh, both of Pa.

[73] Assignee: The United States of America as represented by the United States Department of Energy, Washington, D.C.

[21] Appl. No.: 542,558

[22] Filed: Oct. 18, 1983

Related U.S. Application Data

[63] Continuation-in-part of Ser. No. 310,246, Oct. 9, 1981, abandoned.

[51] Int. Cl.⁴ .............................................. C07C 1/04
[52] U.S. Cl. .................................... 518/715; 502/66; 502/71; 502/74; 502/77
[58] Field of Search ................... 518/715; 502/77, 74, 502/71, 66

[56] References Cited

U.S. PATENT DOCUMENTS

| | | |
|---|---|---|
| 2,496,265 | 2/1950 | Bilisoly . |
| 2,517,036 | 8/1950 | Sensel et al. . |
| 2,637,739 | 5/1953 | McGrath . |
| 3,972,958 | 8/1976 | Garwood et al. . |
| 4,086,262 | 4/1978 | Chang et al. . |
| 4,172,843 | 10/1979 | Dwyer et al. . |
| 4,207,248 | 6/1980 | Butter et al. . |

Primary Examiner—Howard T. Mars
Attorney, Agent, or Firm—Hugh W. Glenn; Robert J. Fisher; Judson R. Hightower

[57] ABSTRACT

Synthesis gas containing CO and $H_2$ is converted to a high-octane hydrocarbon liquid in the gasoline boiling point range by bringing the gas into contact with a heterogeneous catalyst including, in physical mixture, a zeolite molecular sieve, cobalt at 6–20% by weight, and thoria at 0.5–3.9% by weight. The contacting occurs at a temperature of 250°–300° C., and a pressure of 10–30 atmospheres. The conditions can be selected to form a major portion of the hydrocarbon product in the gasoline boiling range with a research octane of more than 80 and less than 10% by weight aromatics.

7 Claims, No Drawings

PROCESS AND CATALYST FOR CONVERTING SYNTHESIS GAS TO LIQUID HYDROCARBON MIXTURE

CONTRACTUAL ORIGIN OF THE INVENTION

The invention described herewith was made in the course of or under a contract with the United States Department of Energy.

BACKGROUND OF THE INVENTION

This is a continuation-in-part of application Ser. No. 310,246, filed Oct. 9, 1981, now abandoned.

The present invention relates to a method for converting synthesis gas containing carbon monoxide and hydrogen to hydrocarbon mixtures suitable for fuel use or as feedstock in petrochemical industries. The invention also relates to catalysts in which mixtures of metals having reductive catalytic activity are dispersed within a crystalline aluminosilicate molecular sieve. In particular the process involves production of high octane, liquid hydrocarbon products that are in the gasoline boiling range. The present catalyst and method selectively produce branched aliphatic hydrocarbons rather than aromatics to obtain a high octane product.

In response to the shortage of petroleum products in the past several years, there has been substantial interest in the conversion of coal to both liquid and gaseous hydrocarbon products. Much work has been done in the area of coal gasification by reaction with water and oxygen to produce carbon monoxide, hydrogen and carbon dioxide as well as of other gases. It is well known that these gasification products can be converted to valued hydrocarbons for use as motor fuels, petrochemical feedstocks and fuel gases.

A detailed treatment of one well known conversion process is given in Storch, *The Fischer-Tropsch and Related Synthesis.* This work describes the use of the various reductive catalytic metals such as cobalt, nickel and iron in mixture with promoters such as thoria, magnesia and manganese and diluent carriers such as kieselguhr, pumice or infusorial earth to convert synthesis gas to a wide range of hydrocarbons. In particular, considerable work was reported involving cobalt catalysts promoted with thoria on amorphous kieselguhr carrier. However, the hydrocarbon product resulting from the use of this catalyst is generally of low octane rating with straight chain aliphatic hydrocarbons constituting the liquids within the gasoline boiling point range. The Fischer-Tropsch process often was regarded as one that could best be used for the production of aliphatic chemicals and special products such as waxes and high grade lubricants rather than fuels.

In recent years there has been considerable interest in the use of zeolite or aluminosilicate molecular sieve supports for Fischer-Tropsch's catalysts. U.S. Pat. No. 4,086,262 suggests the use of a number of zeolites including ZSM-5 having a uniform pore diameter of about 5–6 angstroms as a support for various Fischer-Tropschs catalysts. Catalytic metals including iron, cobalt, nickel, ruthenium, thorium, rhodium, and osmium are suggested. This patent reports the use of a thoria catalyst on acid substituted ZSM-5 zeolite to produce a hydrocarbon product from the conversion of a synthesis gas containing carbon monoxide and hydrogen. This catalyst was used at temperatures above 400° C. to resuly in a liquid product rich in aromatics, but which generally represents a low percentage of the total product.

U.S. Pat. No. 4,207,248 to Butter et al. discloses a method for the conversion of synthesis gas to a liquid hydrocarbon product. The catalyst involves three components including a Fischer-Tropsch component (e.g. cobalt), a zeolite component (e.g. ZSM-5), and a siliceous matrix component relatively free of alumina. This patent teaches that such a catalyst without a promoter (such as thoria) has activity to convert synthesis gas to an olefinic naphtha. Indeed, it is reported that the presence of an alkaline promoter such as thoria actually decreases the activity of the catalyst. The Table following Example 5 of this patent shows a significant loss in carbon monoxide conversion, i.e. 36.8 to 24.1 attributed to the use of a thoria promoter in the catalyst.

Accordingly, it is an object of the present invention to provide a method of producing a high octane liquid hydrocarbon from the conversion of a synthesis gas.

It is a further object to provide a method of converting a major fraction of carbon monoxide and hydrogen in a synthesis gas to an aliphatic hydrocarbon liquid having a major portion thereof as $C_5$ and higher hydrocarbons and with a high research octane number.

It is also an object to provide a catalyst for the reaction of carbon monoxide and hydrogen gases to form liquid hydrocarbons of high research octane rating but with a low aromatic content.

In accordance with the present invention, a method is provided for converting a major fraction of carbon monoxide within a gas mixture including hydrogen and carbon monoxide to produce an aliphatic hydrocarbon product with less than 10% by weight aromatics. The product has a major proportion by weight of $C_5$ and higher hydrocarbons in the gasoline boiling point range with a research octane rating of more than 80. The method includes forming a catalyst consisting essentially of a mixture of cobalt, thoria and a crystalline zeolite having a silica to alumina ratio of about 25–50 and a pore size of 5 to 6 angstroms wherein cobalt is included as 6–20%, thoria is included at 0.5–3% and crystalline zeolite is included at 75–93% by weight. The catalyst is contacted with the gas mixture including carbon and carbon monoxide at a temperature essentially 280° C. at 20–30 atmospheres pressure whereby the aliphatic hydrocarbon product is formed.

DETAILED DESCRIPTION OF THE PREFERRED EMBODIMENT

In preparing the catalyst for the method of the present invention, a solution of soluble cobalt and thorium salts such as nitrates can be prepared in sufficient concentration of each metal to permit inclusion at the desired level in the completed catalyst. The metals can be precipitated as carbonates or other insoluble salts, then after drying, blended with the selected support material. Heating and reduction steps will provide cobalt metal and thorium dioxide (thoria) within the finished catalysts. The cobalt preferably is included in the catalyst at a weight of about 4–10 times that of the thoria. Suitable catalysts for use include about 6–20% by weight cobalt and 0.5–3% by weight thoria, with a preferred range of about 6–14% by weight cobalt and 0.7–2% by weight thoria.

The support material for the catalyst is a crystalline aluminosilicate molecular sieve also known as a zeolite. Such zeolites are described in the published literature and can be prepared by well defined processes, for instance as is presented in U.S. Pat. No. 3,702,886. The zeolite employed in the present catalyst preferably includes pores of uniform diameter of about 5-6 angstroms. It is intended that the catalyst with this support used in accordance with the invention will be selective to the production of aliphatic hydrocarbons in the range of about $C_5$ to $C_{12}$ with substantial branched chains to enhance the octane rating of the liquid product.

The catalytic metals can be incorporated with the zeolite support material in several ways. As suggested the cobalt and thorium can be precipitated from solution as carbonates, dried and calcined to their oxides. The precipitate is crushed, classified to size and blended in a physical mixture with the zeolite in granular form. It is preferred that granules of about 80 micrometers (200 mesh) or less be used for both the metal oxide and zeolite. Alternatively, a solution of the cobalt and thorium soluble salts can be used to permeate into the zeolite which is subsequently dried and heated to a sufficient temperature to convert the catalytic metals to the oxide. In either of these instances aqueous or actone solutions are suitable for preparing the catalyst. Prior to use the colbalt oxide dispersed throughout the zeolite is reduced, with for instance hydrogen gas at a temperature of about 350° C. and a pressure of typically 20 atmospheres to form cobalt metal.

The catalyst as thus described is used in the process of this invention by contacting it with a flow of synthesis gas containing hydrogen and carbon monoxide. It has been found that the temperature of contact is of importance in obtaining a high conversion of carbon monoxide to an aliphatic hydrocarbon liquid within the gasoline boiling range and in obtaining a high proportion of that liquid as branched chain olefins so as to provide a high octane number and thereby increase the value of the product as a fuel for internal combustion engines. For this purpose a contact temperature essentially of 280° C. are required. Reaction temperatures much above this amount not only decrease the total amount of liquid in the product including that within the gasoline boiling range but also increase the aromatic content of the remaining liquid.

As clearly indicated by the Butter et al. patent cited above, a process temperature of only about 260° C. provides only a marginal conversion of carbon monoxide to hydrocarbons. Therefore, it is contemplated that the synthesis gas conversion method of this invention is to be performed at a temperature essentially of 280° C. (i.e. not less than 275° C. or more than 285° C. but in any event not at any temperature which will not achieve a conversion of a major portion of carbon monoxide in the gas feed mixture to an aliphatic hydrocarbon product with less than 10% by weight aromatic content).

Although aromatics can be useful in increasing the octane rating of the fuel, they may carry with them undesirable health effects. It is therefore suggested that the problem of exhaust gas cleanup, may be ameliorated through the selection of branched chain olefins (and possibly pariffins) for imparting high octane characteristics to a liquid hydrocarbon fuel.

In the selection of other process conditions the sythesis gas pressure should be sufficiently high to provide good concentrations of the reactants hydrogen and carbon monoxide in contact with the catalyst but not so high as to raise instrumentation and mechanical problems. Pressures of at least 20 atmospheres are important to provide a good conversion of carbon monoxide and hydrogen to liquid hydrocarbons, however pressures much over 30 atmospheres do not provide sufficient increased performance to economically justify the increased energy and equipment cost. Therefore pressures of 20 to 30 atmosphere are contemplated within the scope of the present invention.

Space velocities of about 500-50,000 gas volumes per hour in respect to the catalyst are typical in processes of this type and can be selected to provide the desired conversion and production.

The heterogeneous catalyst can be contained in a fixed or a fluidized bed while contacting the synthesis gas flow. At the reaction temperatures and pressures, the product stream is a mixture of liquids and gases which can be recovered by well known techniques. The gasoline fraction can be separated from the remaining products in a suitable distilation process.

The following examples are presented as an illustration and comparsion of the present process and catalyst with previous catalysts and methods.

EXAMPLE OF THE INVENTION

A mixture of cobalt and thorium compounds with substantially more cobalt than thorium is precipitated from a nitrate solution by the addition of sodium carbonate followed by heating to a boiling temperature. The precipitate is washed and then dried at about 110° C. The material is crushed to pass through 200 mesh (80 micrometers) and mixed with about 4 weight parts of the zeolite ZSM-5 in granules of about the same size. The resulting mixture was pelletized to about ½ cm diameter pellets. Following calcining and reduction with $H_2$ gas at 350° C., the catalyst prepared in this manner contained about 8-9% by weight cobalt and about 1-2% by weight thoria. About 60 grams of this catalyst was contacted with a continuous flow of synthesis gas containing about a 1:1 $CO/H_2$ ratio at a gas volume hourly space velocity of about 1000, a pressure of about 20 atmospheres and a temperature of 280° C. in a stirred Berty reactor. The resulting product included over 60% by weight $C_5$ and heavier hydrocarbon liquid. About 89% of this liquid was within the gasoline boiling range below about 200° C. while 11% was in the diesel fuel range boiling between about 200°-340° C. The liquid was found to have a research octane number of 86 but with only about 3% by weight aromatics. Additional data respecting the Example along with a second run under similar conditions is given below in Table I. Table I also includes for comparison data from U.S. Pat. No. 4,086,262 (Table I) respecting a thoria and ZSM-5 catalyst in about equal parts used to convert a synthesis gas to hydrocarbons.

TABLE I

| CATALYST | ZSM-5(Co,ThO$_2$) | | ZSM-5 + ThO$_2$ |
|---|---|---|---|
| H$_2$/CO in feed | 1.0 | 1.0 | 1.0 |
| Pressure (PSIG) | 300 | 300 | 1200 |
| Temperature °C. | 280.0 | 279.0 | 426.7 |
| CO Conversion % | 78.3 | 82.2˙ | 22.4 |
| H$_2$ Conversion % | 92.4 | 94.4 | 15.2 |
| Hydrocarbon Product Distribution (wt. %): | | | |
| Methane | 28.2 | 19.8 | 17.3 |
| C$_2$-C$_4$ Hydrocarbons | 10.8 | 10.6 | 73.8 |
| C$_5$+ (Liquid) | 61.0 | 69.6 | 8.9 |
| Aromatics in C$_5$+ | 3.0 | | 41.6 |
| Research Octane No. | 86.0 | | |

It is clear from an examination of Table I that the catalyst and method of the present invention unexpectedly provides a high level of liquid hydrocarbons having a high octane rating without the presence of substantial aromatics. It is also seen that this is advantageously accomplished at less severe temperature and pressure than that employed with the ZSM-5+ThO$_2$ catalyst.

COMPARATIVE EXAMPLE I

Use of Amorphous Support for Cobalt-ThO$_2$ Catalyst

A mixture of cobalt and thoria precipitated from an aqueous solution as in Example 1 was mixed and pelletized with amorphous or poorly crystalline gamma alumina as a support. On carrying out the reaction at 280° C. within a stirred continuous flow Berty reactor it was found that the product included proportionally less hydrocarbon liquid than that obtained with the catalyst of the above Example. In the gasoline boiling range only 68% of the liquid boiled below about 200° C. while 30% boiled in the diesel range of about 200°–340° C. In addition the product included about 10% solid wax material not present with the catalyst illustrated in the Example of the invention. In a nuclear magnetic residence measurement the amount of branch chaining in the liquid product was found to be substantially less than in the product of the above Example leading to the implication of a lower octane number. Additional comparitive data for use of this catalyst with that of the present invention are given below in Table II.

TABLE II

| CATALYST | 10.8% Co, 1.2% ThO$_2$ ZSM-5 | 10.8% Co, 1.2% ThO$_2$ ALUMINA |
|---|---|---|
| Conversion % | | |
| H$_2$ | 93.3 | 91.7 |
| CO | 74.2 | 69.0 |
| Hydrocarbon Product Distribution (wt %): | | |
| Methane | 23.4 | 22.5 |
| C$_2$-C$_4$ | 13.8 | 14.6 |
| C$_5$+ (liquid) | 61.0 | 52.6 |
| Wax | 1.8 | 10.3 |
| Hydrocarbon Liquid Distribution (wt %): | | |
| Gasoline | 89 | 68 |
| Diesel | 11 | 30 |
| Residual (>340° C.) | — | 2 |
| Aromatics | 4 | 2 |
| Olefins | 76 | 43 |
| Saturates | 20 | 55 |

The liquid hydrocarbon product from use of the catalyst of cobalt and thoria on zeolite support is seen to include a high percentage of olefins which on subsequent analyses were found to include to a large degree internal (or B) olefins. Furthermore, the product of this catalyst in accordance with the method of this invention included substantial amounts of branched olefins and paraffins, thus yielding a high research octane number (about 86). In contrast, the product of the catalyst on the alumina support contained a high percentage of straight chain hydrocarbons.

COMPARATIVE EXAMPLE II

Use of Co-ZSM-5 Catalyst

A catalyst containing cobalt on ZSM-5 zeolite but without thoria was prepared as in the proceeding examples. The catalyst was contacted in a stirred Berty reactor with a synthesis gas having a hydrogen to carbon monoxide ratio of about 1 at about 20 atmospheres and a gas volume hourly space velocity of about 1000. Table III below compares the Co-ZSM-5 Catalyst with the catalyst of the present method at a temperature of 260° and 280° C. In addition, data from Examples 2 and 5 of U.S. Pat. No. 4,207,248 are shown for comparison of that prior art process with the Example of the invention.

TABLE III

| | U.S. Pat. No. 4,207,248 | | | | | |
|---|---|---|---|---|---|---|
| Catalyst | Example 2 5.9% CO + HZSM-5 + Silica — Clay hydrogel | Example 5 +1.1% ThO$_2$ + HZSM-5 + Silica — Clay hydrogel | Comparative Example II 6.8% Co + HZSM-5 | | 8.3% Co 1.5% Th + HZSM-5 | Example of the Invention |
| Temp °C. | 263 | 260 | 260 | 280 | 260 | 280 |
| GHSV | 815 | 939 | 980 | 980 | 961 | 961 |
| Pressure (atm) | 14 | 14 | 20 | 20 | 20 | 20 |
| Feed (H$_2$/CO) | 1 | 1 | 1 | 1 | 1 | 1 |
| CO Conversion % | 36.8 | 24.1 | 28.3 | 30.0 | 53.5 | 78.3 |
| H$_2$ Conversion % | 74.3 | 46.6 | 52.7 | 59.6 | 88.1 | 92.4 |
| Product: Liquid Ch$_N$ % (C$_{5+}$) | 71.1 | 70.1 | 58.1 | 34.1 | 66.4 | 61.0 |
| Liquid Product Composition (%): | | | | | | |
| Aromatics | 0.4 | 0.5 | 5.0 | 4.5 | 1.5 | 3.0 |
| Olefins | | | 23.5 | 21.5 | 83.0 | 68.0 |
| Paraffins | | | 71.5 | 74.0 | 15.5 | 29.0 |
| Research Octane No. | | | 37.7 | 59.9 | 62.1 | 86.0 |

The table clearly shows that the catalyst used in accordance with the present invention provides an unexpectedly large quantity of liquid hydrocarbons within the gasoline boiling range and with a high percentage of olefins and a high research octane rating. The side-by-side comparison with U.S. Pat. No. 4,207,248 in Table III also shows that by performing the process at a temperature essentially of 280° C. and a pressure of about 20 atmospheres and above, an unexpected increase in carbon monoxide conversion is obtained.

It is therefore seen that the present invention provides a novel method and catalyst for the selective production of liquid hydrocarbons within the gasoline boiling range having a high octane number without the production of less desirable aromatics.

It will also be clear that although the present invention has been described in terms of specific embodiments and process conditions that one skilled in the art can make various modifications in accordance with the invention as defined in the accompanying claims.

The embodiments of this invention in which an exclusive property or privilege is claimed are defined as follows:

1. A method of converting a major fraction of carbon monoxide within a gas mixture including hydrogen and carbon monoxide to produce an aliphatic hydrocarbon product with less than 10% by weight aromatics, said product having a major proportion by weight of $C_5$ and higher hydrocarbons in the gasoline boiling point range with a research octane rating of more than 80 comprising forming a catalyst consisting essentially of a mixture of cobalt, thoria and crystalline zeolite having a silica to alumina ratio of about 25–50 and a pore size of 5 to 6 angstroms wherein cobalt is included at 6–20%, thoria is included at 0.5–3% and crystalline zeolite is included at 75–93% by weight; and contacting said catalyst with said gas mixture including hydrogen and carbon monoxide at a temperature essentially of 280° C. at 20–30 atmospheres pressure whereby said aliphatic hydrocarbon is formed.

2. The method of claim 1 wherein the catalyst is contacted with the gas mixture at a gas volume space velocity of about 1000 per hour at about 20 atmospheres pressure.

3. The method of claim 1 wherein the catalyst mixture is in the form of pellets of about 0.3–0.7 cm diameter made of compacted granules of less than about 80 micrometers, the granules including granules of crystalline zeolite in mixture with granules of precipitated cobalt and thoria.

4. The method of claim 1 wherein the catalyst mixture includes about 6–14% cobalt and about 0.7–2% thoria by weight.

5. The method of claim 1 wherein the hydrocarbon product is a liquid having a boiling point range of about 200° C. and lower at atmospheric pressure.

6. A catalyst for the conversion of a major fraction of hydrogen and carbon monoxide gases at a temperature essentially of 280° C. at 20–30 atmospheres pressure to a liquid aliphatic hydrocarbon product with less than 10% by weight aromatics, said product having a major proportion by weight of $C_5$ and higher hydrocarbons in the gasoline boiling range with a research octane rating of more than 80, said catalyst consisting essentially of:

a crystalline zeolite molecular sieve having a uniform pore size of about 5–6 angstroms diameter and a silica to alumina ratio of about 25–50;

about 6–20 weight percent cobalt and about 0.5–3 weight percent thoria dispersed throughout about 75–93 weight percent zeolite molecular sieve in physical mixture therewith.

7. The catalyst of claim 6 wherein the catalyst is in the form of pellets of about 0.3–0.7 cm diameter including compacted granules of about 80 micrometers diameter of precipitated cobalt and thoria in mixture with crystalline zeolite.

* * * * *